(12) United States Patent
Epstein

(10) Patent No.: US 10,751,206 B2
(45) Date of Patent: Aug. 25, 2020

(54) CATHETER OR STENT DELIVERY SYSTEM

(71) Applicant: Scott M. Epstein, Boston, MA (US)

(72) Inventor: Scott M. Epstein, Boston, MA (US)

( * ) Notice: Subject to any disclaimer, the term of this patent is extended or adjusted under 35 U.S.C. 154(b) by 194 days.

(21) Appl. No.: 16/101,670

(22) Filed: Aug. 13, 2018

(65) Prior Publication Data

US 2018/0344493 A1 Dec. 6, 2018

Related U.S. Application Data

(63) Continuation-in-part of application No. 14/446,893, filed on Jul. 30, 2014, now Pat. No. 10,568,753,
(Continued)

(51) Int. Cl.
| | |
|---|---|
| *A61F 2/962* | (2013.01) |
| *A61F 2/04* | (2013.01) |
| *A61M 25/01* | (2006.01) |
| *A61M 25/00* | (2006.01) |
| *A61F 2/966* | (2013.01) |

(Continued)

(52) U.S. Cl.
CPC ............... *A61F 2/962* (2013.01); *A61F 2/04* (2013.01); *A61F 2/848* (2013.01); *A61F 2/966* (2013.01); *A61M 25/0068* (2013.01); *A61M 25/01* (2013.01); *A61F 2/97* (2013.01); *A61F 2002/048* (2013.01); *A61F 2002/8486* (2013.01); *A61F 2210/0061* (2013.01); *A61F 2210/0076* (2013.01); *A61F 2230/0039* (2013.01); *A61F 2230/0067* (2013.01); *A61F 2230/0071* (2013.01); *A61F 2230/0076* (2013.01); *A61F 2250/0039* (2013.01); *A61F 2250/0098* (2013.01); *A61M 25/0021* (2013.01);
(Continued)

(58) Field of Classification Search
CPC .......... A61F 2/962; A61F 2/966; A61F 2/848; A61F 2/04; A61F 2/18; A61F 2/95; A61M 25/01; A61M 25/0068
See application file for complete search history.

(56) References Cited

U.S. PATENT DOCUMENTS

| 3,975,350 A | 8/1976 | Hudgin |
|---|---|---|
| 4,026,296 A | 5/1977 | Stoy et al. |
| (Continued) | | |

FOREIGN PATENT DOCUMENTS

WO WO0018446 A1 4/2000

*Primary Examiner* — Richard G Louis
(74) *Attorney, Agent, or Firm* — Intrinsic Law Corp.

(57) ABSTRACT

A method for delivering catheters, and stents composed of soft, compliant polymers through anatomical passages. These devices have a bulbous or enlarged anchorage end with a diameter greater than the rest of the catheter. To facilitate implant and delivery a pusher catheter or sheath with an internal lumen larger than the outer diameter of the catheter but smaller than the outer diameter of the bulbous or enlarged anchorage end is provided. The distal end of pusher catheter or the sheath physically engages the proximal end of the bulbous or enlarged anchorage end and applies an axial force to coaxially advance the catheter over a guidewire through anatomical passages. This method allows a physician to move the catheter to an anatomical site without the device exhibiting buckling due to axial force applied. Similarly, this delivery method will allow more force to be applied to the distal end of the catheter diminishing the likelihood of buckling.

14 Claims, 13 Drawing Sheets

Related U.S. Application Data which is a continuation of application No. 12/824,149, filed on Jun. 26, 2010, now abandoned.

(51) Int. Cl.

| | | |
|---|---|---|
| *A61F 2/848* | (2013.01) | |
| *A61M 25/06* | (2006.01) | |
| *A61M 25/02* | (2006.01) | |
| *A61M 27/00* | (2006.01) | |
| *A61F 2/97* | (2013.01) | |

(52) U.S. Cl.

CPC ... *A61M 27/008* (2013.01); *A61M 2025/0293* (2013.01); *A61M 2025/0681* (2013.01)

(56) References Cited

U.S. PATENT DOCUMENTS

| | | | |
|---|---|---|---|
| 4,475,972 A | 10/1984 | Wong | |
| 4,585,000 A | 4/1986 | Hershenson | |
| 4,610,671 A | 9/1986 | Luther | |
| 4,762,128 A | 8/1988 | Rosenbluth | |
| 4,943,618 A | 7/1990 | Stoy et al. | |
| 5,026,366 A | 6/1991 | Leckrone | |
| 5,135,535 A | 8/1992 | Kramer | |
| 5,149,052 A | 9/1992 | Stoy et al. | |
| 5,405,380 A | 4/1995 | Gianotti et al. | |
| 5,499,975 A | 3/1996 | Cope et al. | |
| 5,499,994 A | 3/1996 | Tihon et al. | |
| 5,601,881 A | 2/1997 | Grimm et al. | |
| 5,603,698 A * | 2/1997 | Roberts | A61F 2/95 604/104 |
| 5,662,703 A | 9/1997 | Yurek et al. | |
| 5,697,948 A | 12/1997 | Marin et al. | |
| 5,785,679 A | 7/1998 | Abolfathi et al. | |
| 6,027,510 A | 2/2000 | Alt | |
| 6,039,694 A | 3/2000 | Larson et al. | |
| 6,143,016 A | 11/2000 | Bleam et al. | |
| 6,280,411 B1 | 8/2001 | Lennox | |
| 6,286,785 B1 | 9/2001 | Kitchen | |
| 6,379,365 B1 | 4/2002 | Diaz | |
| 6,458,156 B1 | 10/2002 | Wan et al. | |
| 6,471,684 B2 | 10/2002 | Dulak et al. | |
| 6,488,802 B1 | 12/2002 | Levingston et al. | |
| 6,547,908 B2 | 4/2003 | Keyes et al. | |
| 6,827,731 B2 | 12/2004 | Armstrong et al. | |
| 6,926,509 B2 | 8/2005 | Nicora et al. | |
| 7,135,015 B2 | 11/2006 | Dulak et al. | |
| 7,316,677 B1 | 1/2008 | Dulak et al. | |
| 7,622,299 B2 | 11/2009 | Sanders et al. | |
| 7,654,989 B2 | 2/2010 | Knapp | |
| 7,655,021 B2 | 2/2010 | Brasington et al. | |
| 7,713,193 B2 | 5/2010 | Nance et al. | |
| 8,048,350 B2 | 11/2011 | Epstein | |
| 8,101,196 B2 | 1/2012 | Luthra et al. | |
| 8,235,968 B2 | 8/2012 | Tremaglio | |
| 8,282,622 B2 | 10/2012 | Dulak et al. | |
| 8,403,890 B2 | 3/2013 | King et al. | |
| 8,491,620 B2 | 7/2013 | Brasington et al. | |
| 8,597,261 B2 | 12/2013 | Knapp | |
| 8,690,936 B2 | 4/2014 | Nguyen et al. | |
| 8,696,550 B2 | 4/2014 | Surti | |
| 8,708,997 B2 | 4/2014 | Parker | |
| 8,709,064 B2 | 4/2014 | Rasmussen et al. | |
| 9,180,028 B2 | 11/2015 | Epstein | |
| 2001/0011164 A1 | 8/2001 | Bierman | |
| 2002/0077592 A1 | 6/2002 | Barry | |
| 2002/0082549 A1 | 6/2002 | Duchamp | |
| 2002/0082638 A1 | 6/2002 | Porter et al. | |
| 2002/0120322 A1 | 8/2002 | Thompson et al. | |
| 2002/0198440 A1 | 12/2002 | Snow | |
| 2003/0021762 A1 | 1/2003 | Luthra et al. | |
| 2003/0040771 A1 | 2/2003 | Hyodoh et al. | |
| 2003/0109899 A1 | 6/2003 | Fisher et al. | |
| 2003/0199993 A1 | 10/2003 | Gellman et al. | |
| 2003/0204238 A1 | 10/2003 | Tedeschi | |
| 2003/0211130 A1 | 11/2003 | Sanders et al. | |
| 2003/0216771 A1 | 11/2003 | Osypka et al. | |
| 2003/0222369 A1 | 12/2003 | Nicora et al. | |
| 2003/0233117 A1 | 12/2003 | Adams et al. | |
| 2004/0010284 A1 * | 1/2004 | Maloof | A61F 9/0017 606/213 |
| 2004/0015224 A1 * | 1/2004 | Armstrong | A61F 2/97 623/1.12 |
| 2004/0111143 A1 * | 6/2004 | Fischell | A61F 2/95 623/1.11 |
| 2004/0143290 A1 | 7/2004 | Brightbill | |
| 2004/0225346 A1 | 11/2004 | Mazumder et al. | |
| 2004/0243158 A1 | 12/2004 | Konstantino et al. | |
| 2005/0038495 A1 | 2/2005 | Greenan | |
| 2005/0049672 A1 | 3/2005 | Murphy | |
| 2005/0149160 A1 | 7/2005 | McFerran | |
| 2005/0182475 A1 | 8/2005 | Jen et al. | |
| 2005/0033343 A1 | 12/2005 | Chermoni | |
| 2006/0095066 A1 | 5/2006 | Chang et al. | |
| 2006/0100664 A1 | 5/2006 | Pai et al. | |
| 2006/0184226 A1 * | 8/2006 | Austin | A61F 2/95 623/1.11 |
| 2007/0010786 A1 | 1/2007 | Casey et al. | |
| 2007/0106361 A1 | 5/2007 | Epstein et al. | |
| 2007/0208373 A1 | 9/2007 | Zaver et al. | |
| 2007/0225659 A1 | 9/2007 | Melsheimer | |
| 2007/0250160 A1 | 10/2007 | Rafiee | |
| 2007/0299422 A1 | 12/2007 | Ignanas et al. | |
| 2008/0255603 A1 | 10/2008 | Naor | |
| 2008/0300629 A1 * | 12/2008 | Surti | A61B 17/0401 606/232 |
| 2009/0112050 A1 | 4/2009 | Farnan et al. | |
| 2009/0299449 A1 | 12/2009 | Styrc | |
| 2010/0022940 A1 | 1/2010 | Thompson | |
| 2010/0057122 A1 | 3/2010 | Campbell et al. | |
| 2011/0153022 A1 | 6/2011 | Singhatat et al. | |
| 2011/0301689 A1 | 12/2011 | Dorn et al. | |

\* cited by examiner

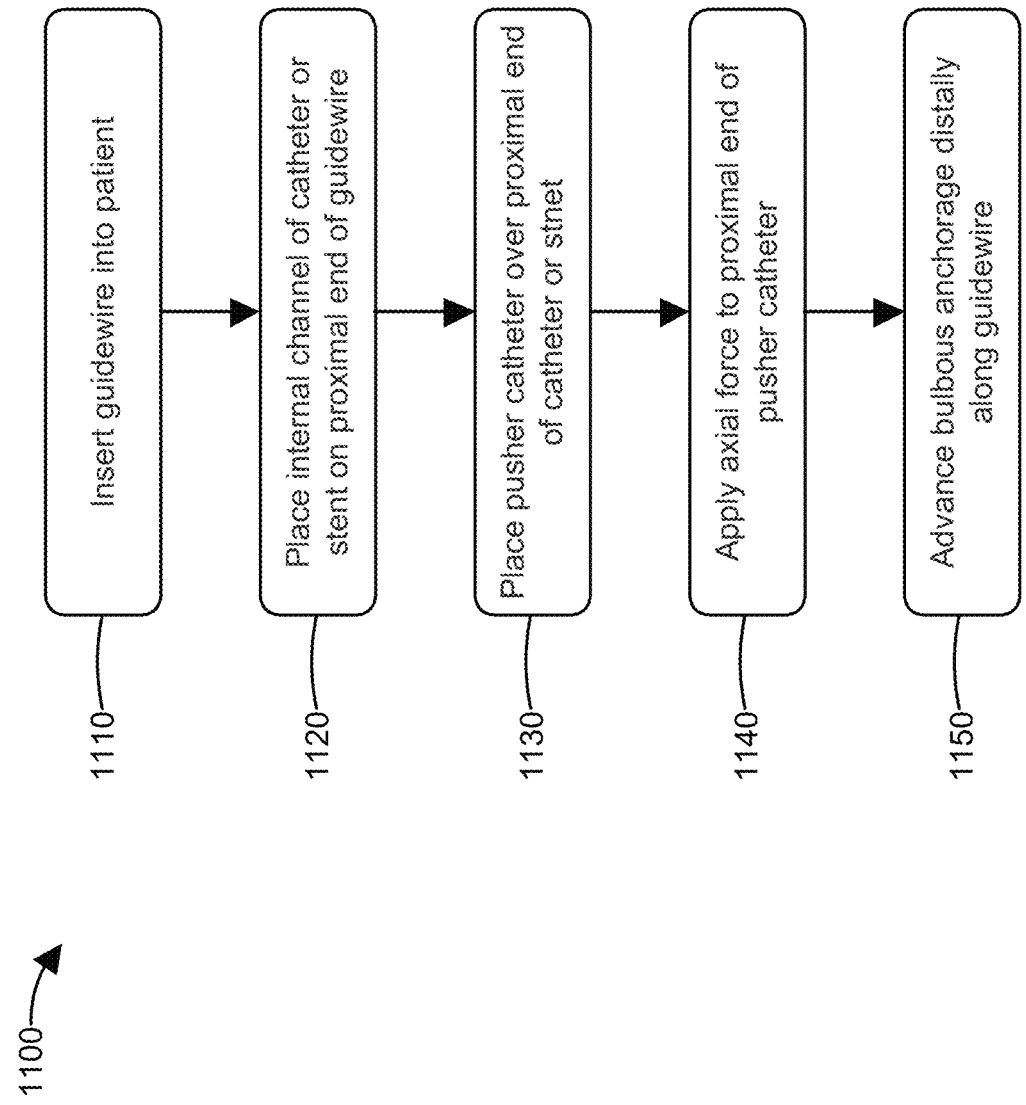

CATHETER OR STENT DELIVERY SYSTEM

CROSS-REFERENCE TO RELATED APPLICATIONS

This application is a continuation-in-part of U.S. patent application Ser. No. 14/446,893, titled "Catheter or Stent Delivery System," filed on Jul. 30, 2014, which is a continuation of U.S. patent application Ser. No. 12/824,149, titled "Catheter Delivery System," filed on Jun. 26, 2010.

FIELD OF INVENTION

The present invention relates to a catheter delivery method and apparatus for delivering catheters or stents, specifically catheters or stents composed of soft, compliant polymers or other suitable materials, through anatomical passages, vascular networks, lumens and cavities.

BACKGROUND OF INVENTION

Specifically-trained physicians often implant a catheter or stent over a guidewire, proximate to, vascular and non-vascular occlusions; or to maintain patency of an anatomical lumen. To implant these devices, a physician must pass the device through vascular and non-vascular anatomical passages and cavities to reach the intended anatomical site which may exhibit an occlusion or an increased resistance when advancing the catheter or stent to the intended location.

One accepted method for passing these devices through anatomical passages includes placing the distal end (defined as the end that is farthest from the Physician) of a guidewire proximate to the anatomical site and advancing the catheter coaxially over the guidewire. In this method, the catheter is pushed from the proximal (defined as the end closest to the Physician) end of the guidewire to the distal end towards the anatomical site. The catheter is advanced either by hand (squeezing the catheter with an index finger and thumb and pushing along) or by using a relatively rigid plastic tube to push the catheter from behind.

In this method, the catheter must be pushed over the guidewire through long, sometimes tortuous, paths, reductions in lumen diameter and anatomical obstructions. Unfortunately, these obstacles require the physician to push the catheter or stent with increasingly excessive axial forces, and depending on the device design or the material from which the device is fabricated, buckling may occur.

Buckling of the device, due to excessive axial forces, is undesired as it may result in a damaged catheter, patient discomfort, accidental perforation of surrounding anatomy and prevention of catheter implantation to its intended location.

The axial load is the maximum force that may be applied to a catheter or stent when advancing the device into a patient before it begins to buckle. Therefore, the axial load is limited by the column strength of the device. This axial load is characterized by the Euler Equation for a simply supported device column under an external axial load (F); wherein (E=modulus of elasticity of the device; I=is the moment of inertia of the cross section of the device; and L=column length of the device). Accordingly, the buckling load of a catheter or stent can be determined by:

$$F=((E)*(I)(3.14)^2)/(L^2)$$

With respect to the Euler Equation, if Length (L), and Moment of Inertia (I) are constant, only a change in materials with an increase in modulus of Elasticity (E) will increase the axial load capacity of a catheter or stent. For example, using the above Euler Equation, pushing a catheter with a length of (0.5 inches (L=0.50 inch)); compared to a catheter with a length of (12 inches (L=12.0 inch)) exhibits a profound effect on the axial load capacity (F). Considering that (L) is raised to the power of (2); it can be seen that (0.50 inches)$^2$ versus (12 inches)$^2$=0.25 versus 144; or a factor of over 500:1. Thus, devices with shorter columns will have a much greater axial load capacity resisting buckling. Unfortunately, shorter catheters are not practical; nor are they typically used in conventional applications where pushing a catheter is the method of delivery.

Multiple techniques have been developed by physicians to prevent buckling of the catheter during implantation. Many of the techniques mentioned below are often combined to reduce catheter buckling.

One technique is for physicians to apply only small amounts of axial force to the catheter either manually (by hand) or with a plastic tube (pusher catheter). This small axial force results in advancing the catheter several millimeters at a time. While this slow advance of the catheter does provide immediate tactile feedback to the physician should the catheter confront an obstruction during advancement, the process is long and tedious. In addition, once the catheter reaches the vascular occlusion at the implantation site, additional axial forces still must be applied in order to push the catheter across the occlusion. This increased axial force often causes the catheter, especially smaller diameter devices, to buckle.

An additional technique to prevent buckling of a catheter during implantation is to use a catheter or stent that is coated with layers of a lubricous polymer. These lubricous polymer coatings, which are typically are very thin, and relatively fragile, reduce the coefficient of friction of the device, which results in a reduced axial load. When these coated devices are inserted and advanced through anatomical paths, they encounter boundaries, such as vessel walls. These coated devices, which are flexible enough to bend tangentially at these boundaries, continue advancing along the anatomical path; however, these tangential bends may add external pressure to the coating at the points of contact. These external pressure points on the device contribute to the aqueous media being squeezed from the coating, much like squeezing water from a sponge. Ultimately, once the coating is compromised, any further contact between the device and anatomical boundaries at these tangential bends will exhibit an increased level of relative friction, such as dry on dry surfaces that results in increased axial loads required to push or advance the catheter along. In addition, this high friction may result in patient discomfort.

A further technique to prevent buckling of the catheter during implantation is to fabricate whole or portions of catheters and stents from moderate to rigid polymers. Similarly, a given thickness of rigid polymer can be extruded while a softer layer is coaxially extruded over or under the more rigid layer. Additionally, a layer of braiding material, either polymeric and or metallic, may be incorporated into the design of a catheter or stent whereby the braid is deposited or sandwiched between layers of catheter material. While these designs are more effective they result in undesirable and uncomfortable products as well as increased manufacturing costs.

Catheters or stents may also be manufactured with rigid portions, such as rigid proximal ends. These more rigid materials often cause patient discomfort and in many cases result in complications due to their increased ability to perforate surrounding anatomy during implantation.

Conventional delivery methods may also include coaxially placing and advancing soft catheters or stents within hollow rigid sheaths, avoiding the need to develop or design catheters that by themselves exhibit superior handling.

In any case, using a sheath or manufacturing a catheter out of more rigid material or incorporating a layer of braiding material are only attempts to increase the column strength of a catheter or stent whereby axial forces and corresponding push-ability can be maximized.

However, using a more rigid material either as part of the catheter, stent or sheath still results in patent pain and or discomfort.

As mentioned previously, many of the techniques mentioned above are often combined to reduce catheter buckling. For instance, in an attempt to augment conventional sheath-over-catheter delivery methods, catheters may be coaxially braided, a more rigid layer maybe integrated, and/or the device may be coated with layers of lubricous polymer. However, even a combination of these techniques results in patient discomfort, slow advancement and eventual buckling of the catheter or stent when increased axial loads are required to advance into or through anatomical passages.

Therefore, embodiments of the invention establish a novel method for delivery of catheters and stents that overcomes the buckling phenomena.

SUMMARY OF INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An aspect of the subject invention discloses a method for delivering a catheter or stent to an anatomical site, the method comprising: a) inserting a guidewire into a patient, such that a distal end of the guidewire is proximal to the anatomical site and a proximal end of the guidewire is accessible to a user; b) placing a catheter with an internal channel with a first opening on the distal end and a second opening on a proximal end over the guidewire such that the guidewire is contained within the internal channel, wherein the proximal end of catheter comprises a first external diameter and the distal end comprises a second external diameter, further wherein the second external diameter is larger than the first external diameter such that the distal end of the catheter comprises a proximal external contacting surface; c) placing a tube, sheath, or Pusher catheter with a distal opening and an internal channel over the proximal end of the catheter, wherein the diameter of the distal opening and the internal channel is larger than the first external diameter, but smaller than the second external diameter, further wherein the tube, sheath, or Pusher catheter comprises a distal contacting surface and a proximal pushing surface; d) pushing the tube, sheath, or Pusher catheter over the catheter until the distal contacting surface of the tube engages the proximal external contacting surface of the catheter; e) applying axial force to the proximal pushing surface of the tube, sheath, or Pusher catheter such that it advances the catheter on the guidewire; f) stopping step e) once the catheter or stent is positioned in the anatomical site; and g) removing the tube, sheath or pusher catheter and leaving the catheter or stent in place.

Another aspect of the subject invention is a catheter delivery system comprising: a catheter with an internal channel with a first opening on the distal end and a second opening on a proximal end, wherein the proximal end of catheter comprises a first external diameter and the distal end comprises a second external diameter, further wherein the second external diameter is larger than the first external diameter such that the distal end of the catheter comprises a proximal external contacting surface; a tube with a distal opening, a distal contacting surface and an internal channel, wherein the diameter of the distal opening and the internal channel is larger than the first external diameter of the catheter, but smaller than the second external diameter; wherein the proximal end of the catheter is place into the distal opening of the tube until the distal contacting surface engages the proximal external contacting surface, further wherein the tube pushes the catheter such that both advance over a guidewire that is inserted into a patient such that a distal end of the guidewire is proximal to an anatomical site.

In one embodiment of the subject invention, the shape of the internal channel of the tube, sheath, or Pusher catheter complements the external shape of the proximal end of the catheter.

In another embodiment of the subject invention, the catheter has a cross-sectional shape that is substantially circular, triangular, square, oval, trapezoidal, hexagonal or octagonal.

In an additional embodiment of the subject invention, the shape of the internal channel of the tube, sheath, or pusher catheter has a cross-sectional shape that is substantially circular, triangular, square, oval, trapezoidal, hexagonal or octagonal.

In a further embodiment of the subject invention, the tube, sheath, or pusher catheter comprises substantially resilient material.

In one embodiment of the subject invention, the distal end of the catheter is a bulbous or enlarged anchorage end.

In another embodiment of the subject invention, the catheter comprises, consists of, or consists essentially of a soft compliant material, such as structural hydrogel.

In one embodiment of the subject invention, the method does not require that the guidewire be hydrophilically coated to exhibit a reduction in forces.

In another embodiment of the subject invention, the catheter has at least one port hole proximal to the distal end.

In an additional embodiment of the subject invention, the distal end of the catheter has a profile that is selected from the group consisting of substantially spherical, substantially oval, substantially barbell, substantially trumpet or substantially conical.

Another aspect of the invention is directed to a catheter or stent delivery system. The catheter or stent delivery system comprises: a catheter or stent comprising: an elongated cylindrical portion having a first diameter; a bulbous or enlarged anchorage having a second diameter greater than the first diameter, the bulbous or enlarged anchorage disposed at a distal end of the elongated cylindrical portion; and an internal channel extending along a channel axis from a proximal end of the elongated cylindrical portion to a distal end of the bulbous or enlarged anchorage. The catheter or stent delivery system also comprises: a pusher tube having an internal lumen, the internal lumen having an internal diameter greater than the first diameter but less than the second diameter. The elongated cylindrical portion is disposed in the internal lumen of the pusher tube, and a wall on a distal end of the pusher tube physically engages a proximal end of the bulbous or enlarged anchorage, such that an axial force at a proximal end of the pusher tube causes the bulbous or enlarged anchorage to advance distally.

In one or more embodiments, the bulbous or enlarged anchorage has a shape selected from the group consisting of: substantially spherical, substantially ovoid, substantially barbell, substantially trumpet-shaped, and substantially conical. In one or more embodiments, the delivery system is disposed in a sheath. In one or more embodiments, a distal end of the sheath includes axial slits. In one or more embodiments, the axial slits are configured to open in response to the distal advancement of the bulbous or enlarged anchorage. In one or more embodiments, the elongated cylindrical portion comprises an anchor portion disposed at the proximal end of the elongated cylindrical portion, the anchor portion configured to anchor a proximal end of the catheter or stent in an anatomical cavity. In one or more embodiments, port holes are defined in a distal end of the elongated cylindrical portion proximal to the bulbous or enlarged anchorage. In one or more embodiments, the catheter or stent comprises hydrogel polymer layers.

Another aspect of the invention is directed to a catheter or stent delivery system. The catheter or stent delivery system comprises: a catheter or stent comprising: an elongated cylindrical portion having a first external diameter; and a bulbous or enlarged anchorage having a second external diameter greater than the first external diameter, the bulbous or enlarged anchorage disposed at a distal end of the elongated cylindrical portion. The catheter or stent delivery system also comprises a cylindrical pusher catheter having a third external diameter less than the second external diameter; an internal channel extending along a channel axis from a proximal end of the cylindrical pusher catheter to a distal end of the bulbous or enlarged anchorage; a sheath having a sheath internal diameter greater than the first and third external diameters but less than the second external diameter. The cylindrical pusher catheter and the elongated cylindrical portion are disposed in the sheath such that a distal end of the cylindrical pusher catheter physically engages a proximal end of the elongated cylindrical portion, such that an axial force at a proximal end of the cylindrical pusher catheter causes the bulbous or enlarged anchorage to advance distally.

In one or more embodiments, the bulbous or enlarged anchorage has a shape selected from the group consisting of: substantially spherical, substantially ovoid, substantially barbell, substantially trumpet-shaped, and substantially conical. In one or more embodiments, a distal end of the sheath includes axial slits. In one or more embodiments, the axial slits are configured to open in response to the distal advancement of the bulbous or enlarged anchorage. In one or more embodiments, the elongated cylindrical portion comprises an anchor portion disposed at the proximal end of the elongated cylindrical portion, the anchor portion configured to anchor a proximal end of the catheter or stent in an anatomical cavity. In one or more embodiments, port holes are defined in a distal end of the elongated cylindrical portion proximal to the bulbous or enlarged anchorage. In one or more embodiments, the catheter or stent comprises hydrogel polymer layers.

Another aspect of the invention is directed to a method for delivering a catheter or stent to an anatomical site. The method comprises: a) inserting a guidewire into a patient, such that a distal end of the guidewire is proximal to the anatomical site and a proximal end of the guidewire is accessible to a user; b) placing an internal channel of the catheter or stent on the proximal end of the guidewire; c) placing a pusher tube over a proximal end of the catheter or stent, the pusher tube having an internal lumen, the internal lumen having an internal diameter greater than the first diameter but less than the second diameter; d) applying an axial force to a proximal end of the pusher tube, the axial force causing a wall on a distal end of the pusher tube to physically engage a proximal end of the bulbous or enlarged anchorage, such that the axial force at the proximal end of the pusher tube causes the bulbous or enlarged anchorage to advance distally along the guidewire. The catheter or stent comprises: an elongated cylindrical portion having a first diameter; a bulbous or enlarged anchorage having a second diameter greater than the first diameter, the bulbous or enlarged anchorage disposed at a distal end of the elongated cylindrical portion; and the internal channel extending along a channel axis from a proximal end of the elongated cylindrical member to a distal end of the bulbous or enlarged anchorage.

In one or more embodiments, the method further comprises stopping the axial force when the catheter or stent is positioned proximal to the anatomical site. In one or more embodiments, the method further comprises removing the pusher tube. In one or more embodiments, the method further comprises disposing the catheter or stent in a sheath.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of exemplary embodiments thereof, which description should be considered in conjunction with the accompanying drawings, in which:

FIG. 11 is a flow chart of a method for delivering a catheter or stent to an anatomical site.

DETAILED DESCRIPTION OF PREFERRED EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive of, but not limited to, the following appended claims as set forth.

Aspects of the subject invention are directed to a novel method for delivery of catheters and stents to anatomical sites that prevents, or reduces the likelihood of, buckling of the device due to applied axial force. Specifically, for applications where a flexible catheter is made of a soft or pliable material having material properties and having an elongated dimension that would not sustain axial forces to push said soft or pliable flexible catheter into an anatomical lumen to a target site in a patient, this invention provides a pusher tube into which the soft or pliable or flexible catheter or stent is placed. The soft, pliable and flexible catheter is provided with an enlarged or bulbous terminal end at a distant end thereof (the end inserted into the patient). A distal end of the pusher tube being in contact with the enlarged terminus of the flexible catheter or stent, so that the pusher tube can be used to exert axial force directly onto the enlarged terminus of the flexible catheter or stent and to push the catheter or stent into the patient against the force of friction (from the walls of the patient's lumen) and overcoming the buckling forces that would otherwise frustrate the pushing of the flexible (floppy) catheter or stent into such patient lumen space, especially over longer distances or depths. Specifically, if the flexible catheter or stent has a geometry and elongated form factor such that given its material properties it would buckle under the Euler formula and forces described above, the pusher tube would transfer the user's axial pushing force from the proximal end of the system into the distal end of the system, in effect applying said axial inward pushing force at the distal (deep) end of the flexible catheter or stent rather than at its exposed (proximal) end, thereby avoiding or reducing its tendency to buckle.

Figure 1:
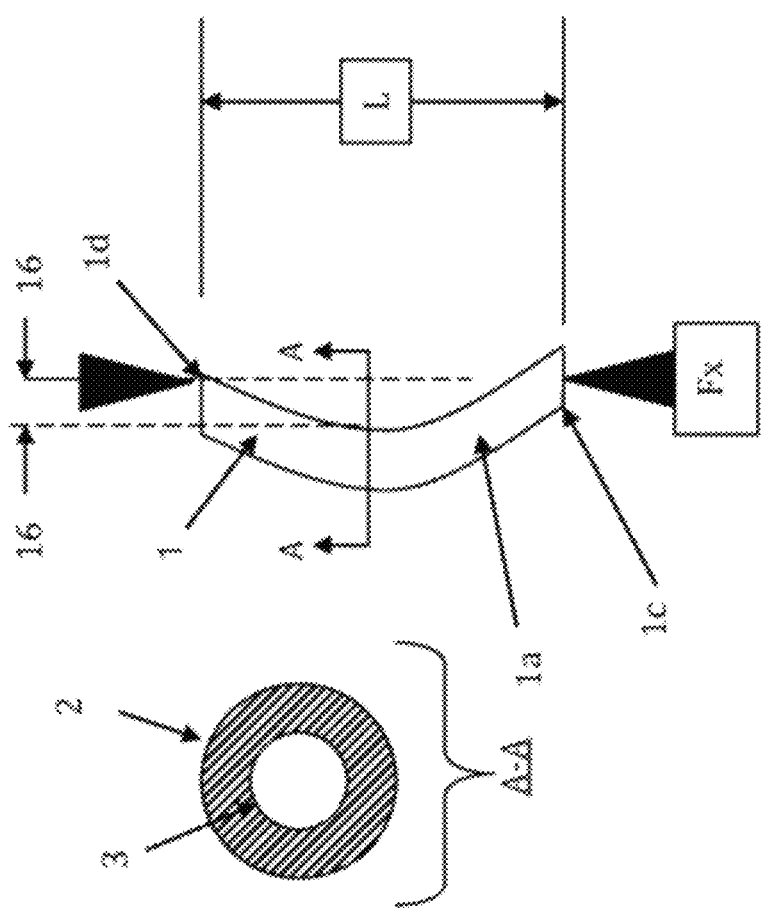
FIG. 1 illustrates a top view and a cross-sectional view of a catheter or stent with simple column catheter shaft with a given length that is subjected to an axial force.
Figure 2:
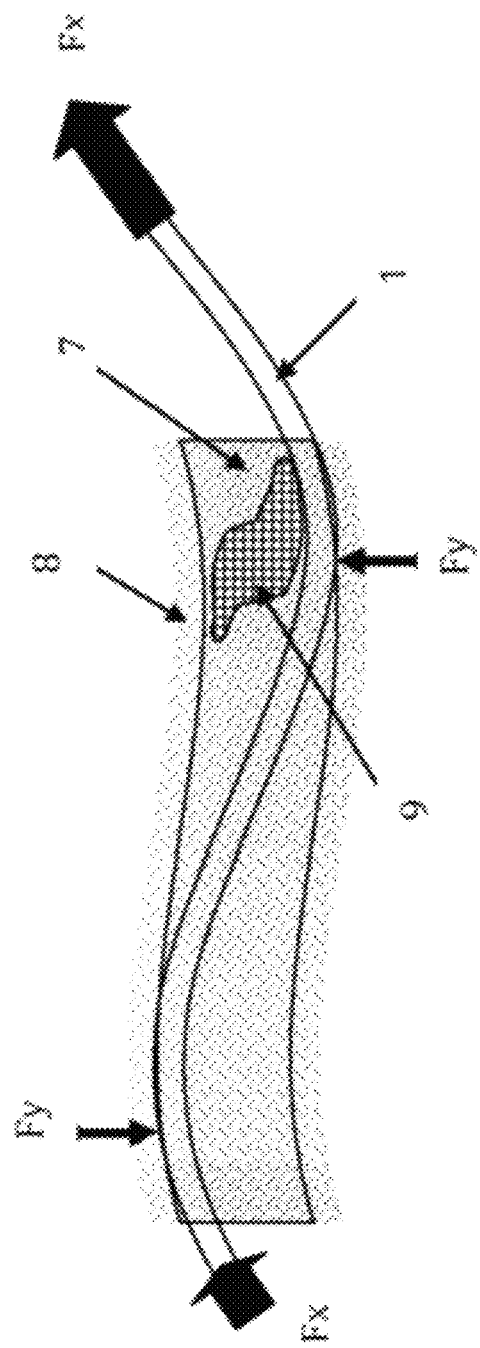
FIG. 2 illustrates a cross-sectional top view of a catheter passing through anatomical lumens upon application of axial force.

FIG. 1 is a diagram illustrating a top view and a cross-sectional view of a catheter or stent (1) with simple column catheter shaft (1a) with a given length (L). An axial force (Fx) may be applied to either the proximal end (1c) of catheter (1) by a physician, the distal end (1d) by an anatomical obstruction, or both when the physician continues to push the catheter (1) once it encounters an anatomical obstruction. As shown in FIG. 2, catheter (1) passes through anatomical lumens (7) upon application of axial force (Fx) to the proximal end of the catheter.

During this passage, the catheter (1) may often contact a wall or peripheral structure (8) of lumen (7) or an obstruction (9). Once this contact occurs, a resulting force (Fy) may be applied to the catheter (1) at tangent points, requiring the application of additional axial force (Fx) to continue advancing the catheter (1) to its intended location.

As shown in FIGS. 1 and 2, the axial force Fx applied to catheter (1) is greater than the axial load, causing the catheter to buckle. Lines (16) illustrate the original position of catheter shaft (1a) prior to buckling.

FIG. 1 further illustrates a cross-sectional view of catheter shaft (1a) delineated by line A-A. Catheter shaft (1a) comprises an outer diameter (2) and an inner diameter (3). Diameters (2) and (3) are used to calculate Moment of Inertia (I) for the Euler Equation.

Figure 9:
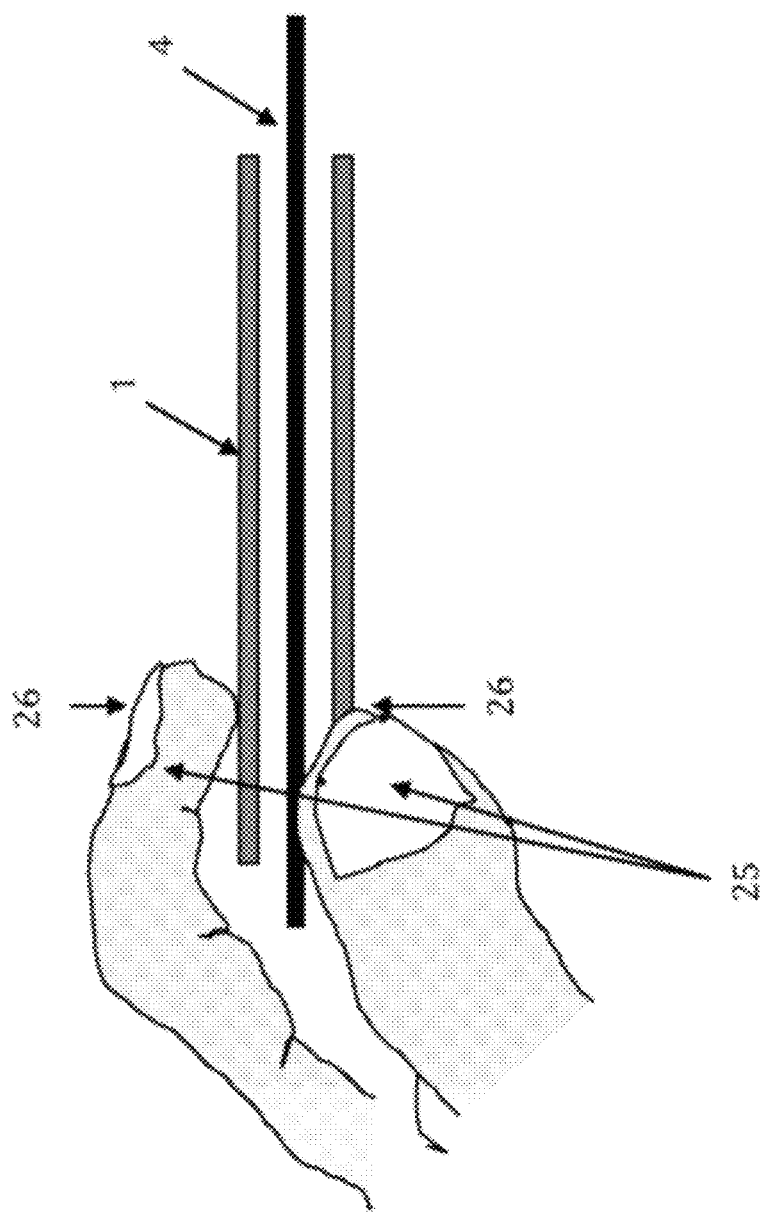
FIG. 9 illustrates a top cross-sectional view of a catheter being pushed by hand over a guidewire.

FIG. 9 illustrates a method of implanting a catheter (1) by squeezing (26) the catheter (1) with a hand (25) and manually advancing the catheter (1) over a guidewire (4) by applying an axial force to coaxially advance the catheter over the guidewire (4) in a distal direction through anatomical passages (not shown).

Figure 3:
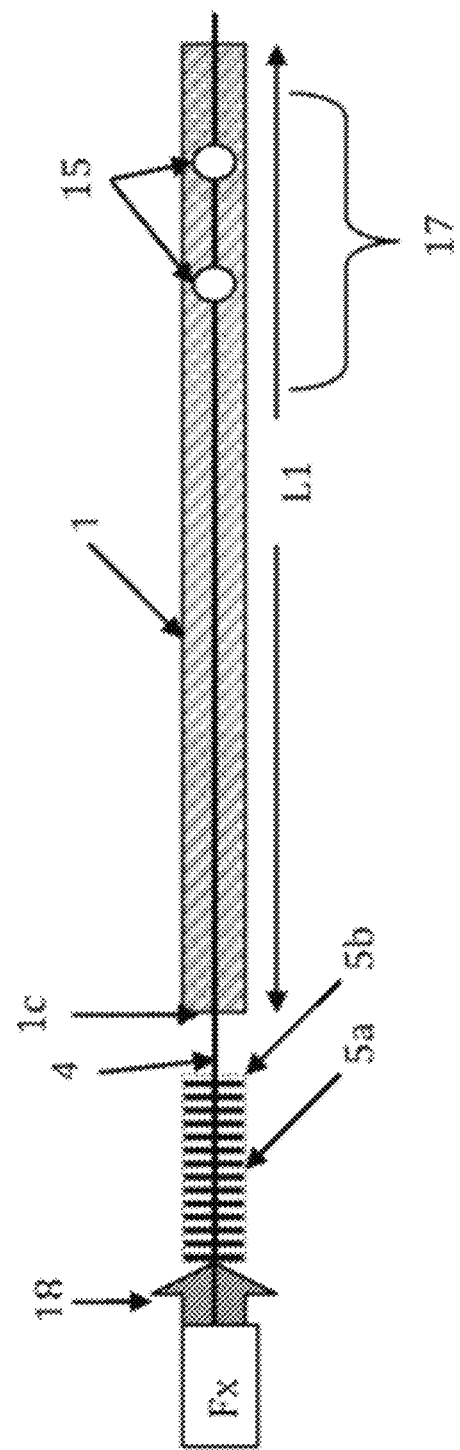
FIG. 3 illustrates a top view of a conventional method of implanting a catheter of length.

FIG. 3 illustrates a conventional method of implanting a catheter (1) of length (L1). Catheter (1) is coaxially slid over a guidewire (4). A distal end (5b) of a pusher catheter (5a) physically engages the proximal end (1c) of the catheter (1) and applies an axial force (Fx) to coaxially advance the catheter over the guidewire (4) in a distal direction (18) through anatomical passages (not shown).

In this conventional method, pusher catheter (5a) has an internal lumen (not shown) with an internal diameter that is large enough to allow the guidewire (4) to pass through pusher catheter (5a) as it advances; however, this internal lumen diameter is smaller than outer diameter (2) (e.g., as illustrated in FIG. 1) of catheter (1) to allow the distal end (5b) of pusher catheter (5a) to engage the proximal end (1c) of the catheter (1).

FIG. 3 further illustrates two catheter port holes (15) located proximal to the distal end of the catheter (1). These port holes (15) in conventional catheters are designed to increase fluid transfer within the catheter. However, these port holes (15) often result in increased likelihood of buckling, as shown as the likely buckling point (17).

Figure 4:
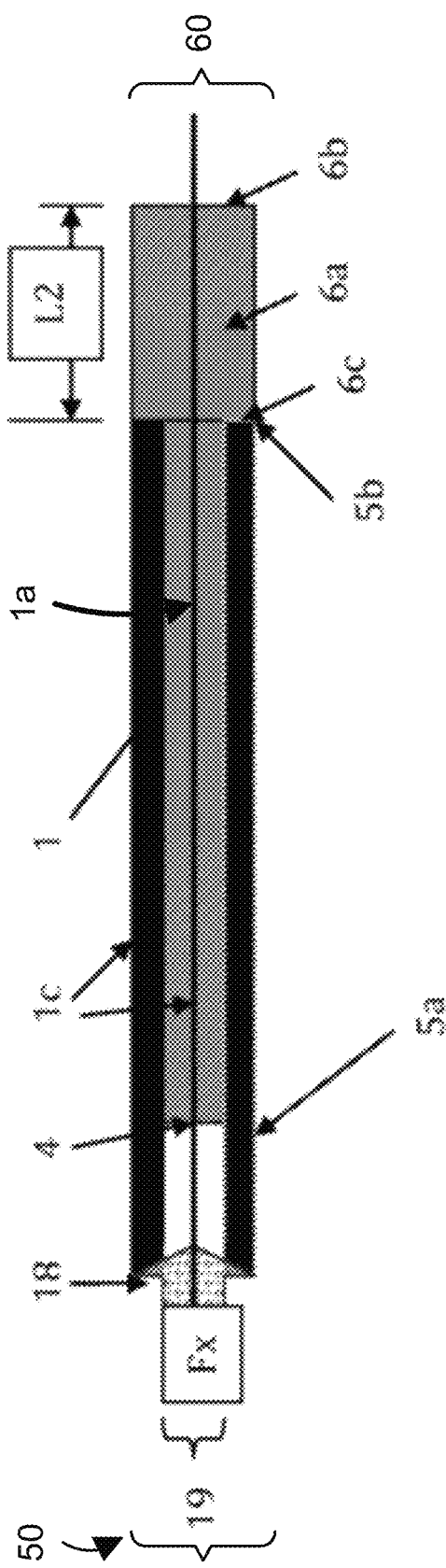
FIG. 4 illustrates a top cross-sectional view of a catheter with a bulbous or enlarged anchorage end being pushed over a guidewire by the physical engagement of the distal end of a pusher catheter and the proximal end of the bulbous or enlarged anchorage end.

FIG. 4 illustrates an embodiment of a method of the subject invention. A catheter or stent (1) is coaxially slid over the guidewire (4). In this embodiment, the catheter (1) has a bulbous or enlarged anchorage end (6a). The bulbous or enlarged anchorage end (6a) has a distal end (6b) and a proximal end (6c) separated by a length (L2). The bulbous or enlarged anchorage end (6a) has an outer diameter that is greater than the outer diameter (2) of the shaft (1a) of catheter (1). The outer diameter (60) of the bulbous or enlarged anchorage end (6a) is uniform or substantially uniform across the distal end (6b) to the proximal end (6c)

of the bulbous or enlarged anchorage end (6a) in the embodiment illustrated in FIG. 4 (e.g., the bulbous or enlarged anchorage end (6a) can have a cylindrical shape defined by its outer diameter and its length (L2)). For example, the outer diameter (60) of the bulbous or enlarged anchorage end (6a), from the distal end (6b) to the proximal end (6c), can be equal to or substantially equal to the outer diameter (50) of the pusher catheter (5a) (e.g., as illustrated in FIG. 4). In other embodiments, the outer diameter (60) of the bulbous or enlarged anchorage end (6a), from the distal end (6b) to the proximal end (6c), can be greater than the outer diameter (50) of the pusher catheter (5a). For example, the bulbous or enlarged anchorage end (6a) can have a uniform or a substantially uniform outer diameter (60), from the distal end (6b) to the proximal end (6c), that is greater than the outer diameter (50) of the pusher catheter (5a). In another example, the outer diameter (60) of the bulbous or enlarged anchorage end (6a) can be greater than the outer diameter (50) of the pusher catheter (5a), but the outer diameter (60) of the bulbous or enlarged anchorage end (6a) can be variable between the distal end (6b) and the proximal end (6c).

In this embodiment, the pusher catheter (5a) has an internal lumen (not shown) with an internal diameter (19) that is large enough to allow the guidewire (4) and the outer diameter (2) of the shaft (1a) of catheter (1) to pass through pusher catheter (5a) as it advances. However, this internal lumen diameter is smaller than the outer diameter (60) of the bulbous or enlarged anchorage end (6a) of catheter (1). Thus, the distal end (5b) of pusher catheter (5a) physically engages the proximal end (6c) of the bulbous or enlarged anchorage end (6a) and applies an axial force (Fx) to coaxially advance the catheter (1) over the guidewire (4) in a distal direction (18) through anatomical passages (not shown). In this manner only a short column length (L2) of the bulbous or enlarged anchorage end (6a) of catheter (1) has an axial load applied to it, a critical variable in column strength analysis. By only applying axial force (Fx) to the proximal end (6c) of the bulbous or enlarged anchorage end (6a), the effective column length of the catheter (1) is reduced to the short column length (L2) of the bulbous or enlarged anchorage end (6a) of catheter (1).

This physical engagement between the distal end (5b) of pusher catheter (5a) and the proximal end (6c) of the bulbous or enlarged anchorage end (6a) diminishes the likelihood of buckling compared to a similar axial force applied to the proximal end (1c) as shown in FIG. 3. Since this method allows the application of additional axial force without buckling, a physician may push catheter (1) through an obstruction. Accordingly, the disclosed delivery method is a universal system which can be used on any catheter or stent with a distal end that has a diameter greater than the shaft diameter of the device. This system diminishes the need for thicker, more rigid catheters. Furthermore, the disclosed invention improves the implantation of catheters and stents comprised of sufficiently soft durometer materials or catheters and stents with ratios of inner diameters and outer diameters that diminish catheter column strength.

This method allows a physician to move the catheter to an anatomical site with less applied axial force over a guidewire since the catheter has less resistance. This method allows a physician to push a relatively short length of catheter rather than a long length. This delivery method will allow more force to be applied to the short distal end of the catheter while diminishing the likelihood of buckling.

In one embodiment of the subject invention, the catheter (1) may have port holes, similar to those shown in FIG. 3, on the shaft (1a) immediately proximal (not shown) to the bulbous or enlarged anchorage end (6a) that do not affect buckling of the device. In this embodiment, the internal lumen of the pusher catheter (5a) will pass over the port holes contained on the outer diameter (2) of the shaft (1a) of catheter (1) to physically engage the proximal end (6c) of the bulbous or enlarged anchorage end (6a).

Figure 5:
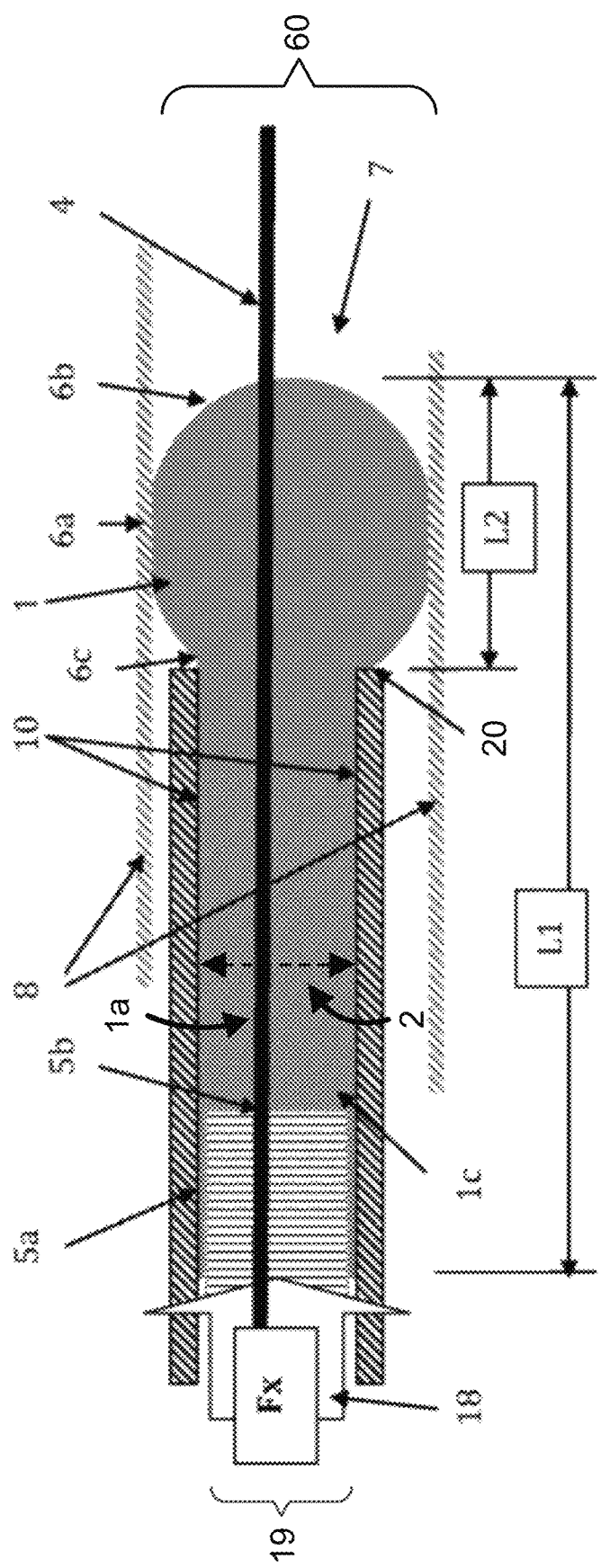
FIG. 5 illustrates a top cross-sectional view of a catheter with a bulbous or enlarged anchorage end being pushed out of a sheath over a guidewire by the physical engagement of the distal end of a pusher catheter and the proximal end of the bulbous or enlarged anchorage end.

FIG. 5 illustrates another embodiment of a method of the subject invention. In this embodiment, a catheter or stent (1) is coaxially slid over the guidewire (4). The catheter (1) has a bulbous or enlarged anchorage end (6a) in the shape of a sphere or other suitable shape defined by the outer diameter (60) of the bulbous or enlarged anchorage end (6a). The bulbous or enlarged anchorage end (6a) has a distal end (6b) and a proximal end (6c) separated by a length (L2). The outer diameter (60) of the bulbous or enlarged anchorage end (6a) is greater than outer diameter (2) of the shaft (1a) of the catheter (1) such that a distal end (20) of sheath (10) can physically engage the proximal end (6c) of the bulbous or enlarged anchorage end (6a). As shown, the outer diameter (2) of the shaft (1a) of the catheter (1) is contained within a sheath (10) and the bulbous or enlarged anchorage end (6a) is not contained within the sheath (10). To facilitate delivery of the catheter (1) through anatomical obstructions (illustrated by lumen (7) surrounded by walls (8)), the outer diameter (2) of the shaft (1a) and bulbous or enlarged anchorage end (6a) of the catheter (1) are both initially contained within sheath (10) (not shown). Once the anatomical site is reached, a distal end (20) of sheath (10) physically engages the proximal end (6c) of the bulbous or enlarged anchorage end (6a) while within the sheath (10) and applies an axial force (Fx) to coaxially advance the catheter (1) over the guidewire (4) in a distal direction (18) to push the catheter (1) out of the distal end (20) of the sheath (10) into lumen (7). The pusher catheter (5a) has an internal lumen (not shown) with an internal diameter (19) that is large enough to allow the guidewire (4) to pass through pusher catheter (5a) as it advances. In another embodiment of the subject invention, distal end (5b) of pusher catheter (5a) may also physically engage the proximal end (1c) of the catheter (1) and apply an axial force (Fx) to coaxially advance the catheter (1) over the guidewire (4) out through the distal end (20) of sheath (10) once the anatomical site is reached.

Figure 6:
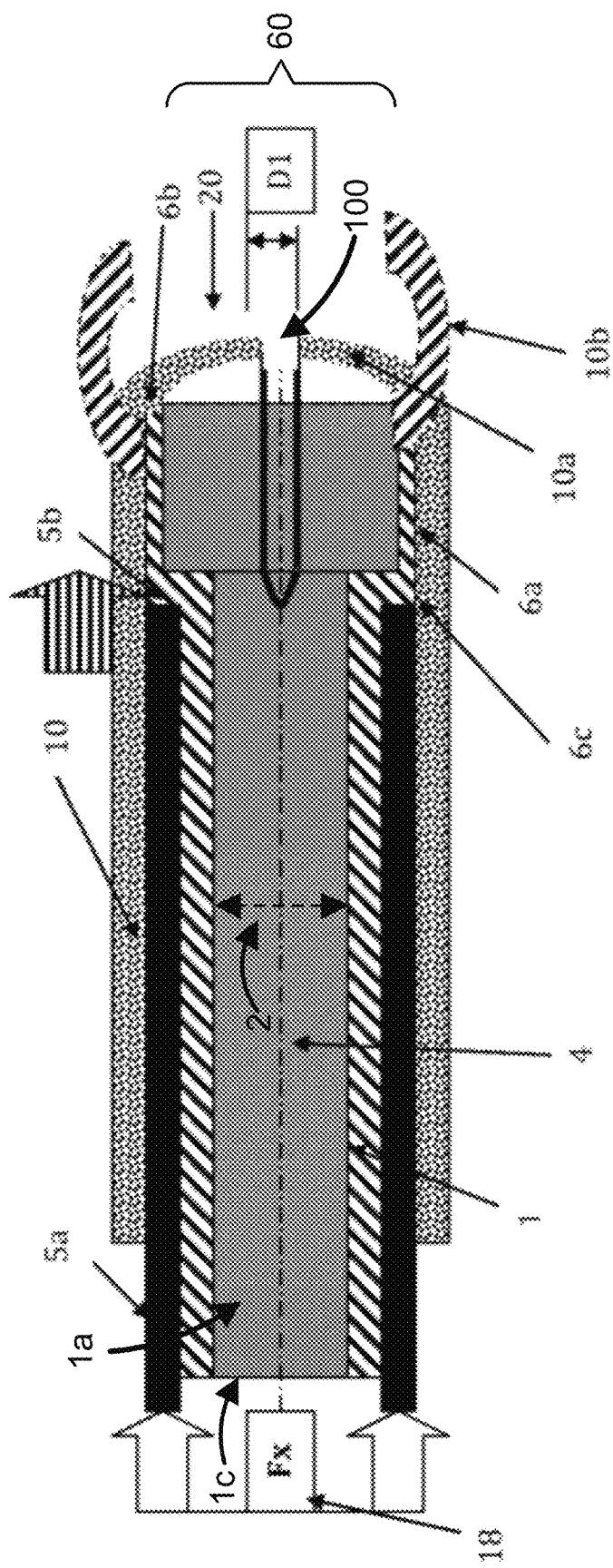
FIG. 6 illustrates a top cross-sectional view of a catheter with a bulbous or enlarged anchorage end and a pusher catheter contained within a sheath that comprises a substantially spherical distal end that remains closed to facilitate advancement through anatomical obstructions, wherein once the desired site is reached, the distal end of a pusher catheter engages the proximal end of the bulbous or enlarged anchorage end to push the catheter out of the distal end of the sheath.

FIG. 6 illustrates an alternative embodiment of a method of the subject invention. In this embodiment, a catheter or stent (1) has a bulbous or enlarged anchorage end (6a) with a distal end (6b) and a proximal end (6c). The bulbous or enlarged anchorage end (6a) has an outer diameter that is greater than outer diameter (2) of the shaft (1a) of catheter (1). A pusher catheter (5a) has an internal lumen (not shown) with an internal diameter that is large enough to allow the outer diameter (2) of the shaft (1a) of catheter (1) to pass through pusher catheter (5a) as it advances. However, this internal lumen diameter is smaller than the outer diameter (60) of the bulbous or enlarged anchorage end (6a) of catheter (1). Thus, the distal end (5b) of pusher catheter (5a) physically engages the proximal end (6c) of the bulbous or enlarged anchorage end (6a). The shaft (1a) of catheter (1) and the bulbous or enlarged anchorage end (6a) are both coaxially slid and contained within sheath (10). Sheath (10) has a closed end (10a) with axial slits (100) of a corresponding thickness (D1). The catheter (1), the pusher catheter (5a) and the sheath (10) are all coaxially slid over a guidewire (4). The distal end (5b) of pusher catheter (5a) physically engages the proximal end (6c) of the bulbous or enlarged anchorage end (6a) and applies an axial force (Fx) to coaxially advance the catheter (1) and the sheath (10) over the guidewire (4) in a distal direction (18). Once the anatomical site is reached, the distal end (5b) of pusher catheter (5a) physically engages the proximal end (1c) of the catheter (1) and applies an axial force (Fx) to coaxially advance the catheter (1) over the guidewire (4) out through sheath (10). The axial slits open (10b) to allow catheter or stent (1) to coaxially slide over the guidewire (4) and through sheath (10). A pusher catheter (5a) within a sheath (10) with a closed end adds greater stability when pushing the catheter through difficult and occluded passages.

Figure 7A:
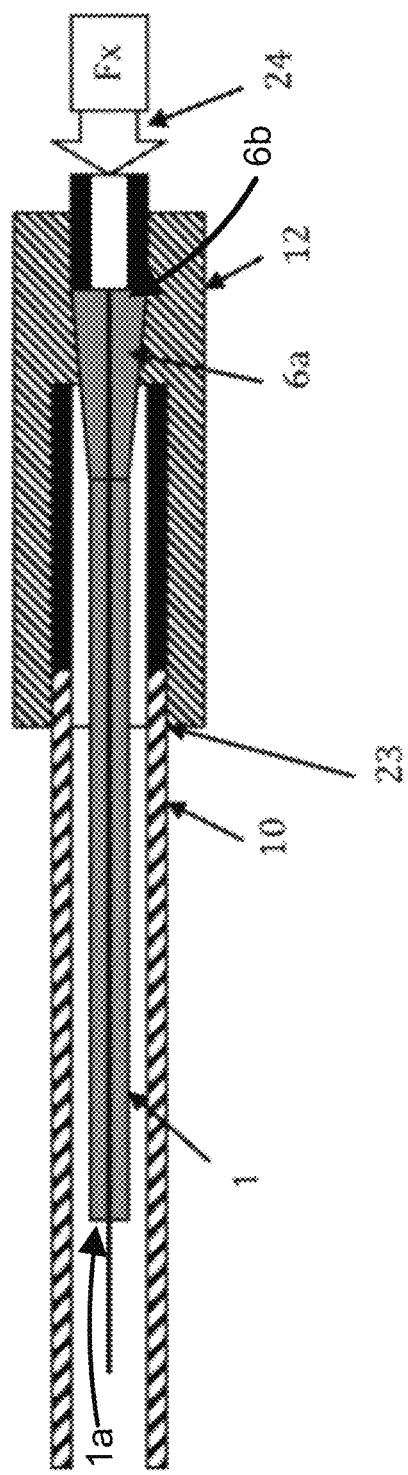
FIGS. 7A, 7B, and 7C illustrate a top cross-sectional view of a catheter with a bulbous or enlarged anchorage end being pushed out of a sheath over a guidewire by the physical engagement of the distal end of a pusher catheter and the proximal end of the bulbous or enlarged anchorage end.
Figure 7B:
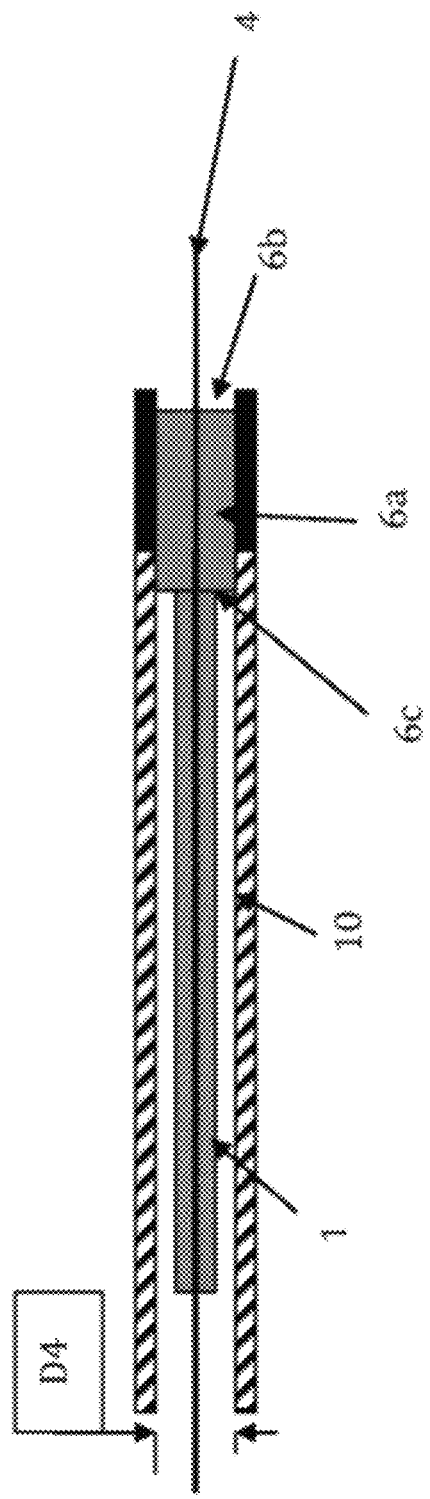
Figure 7C:
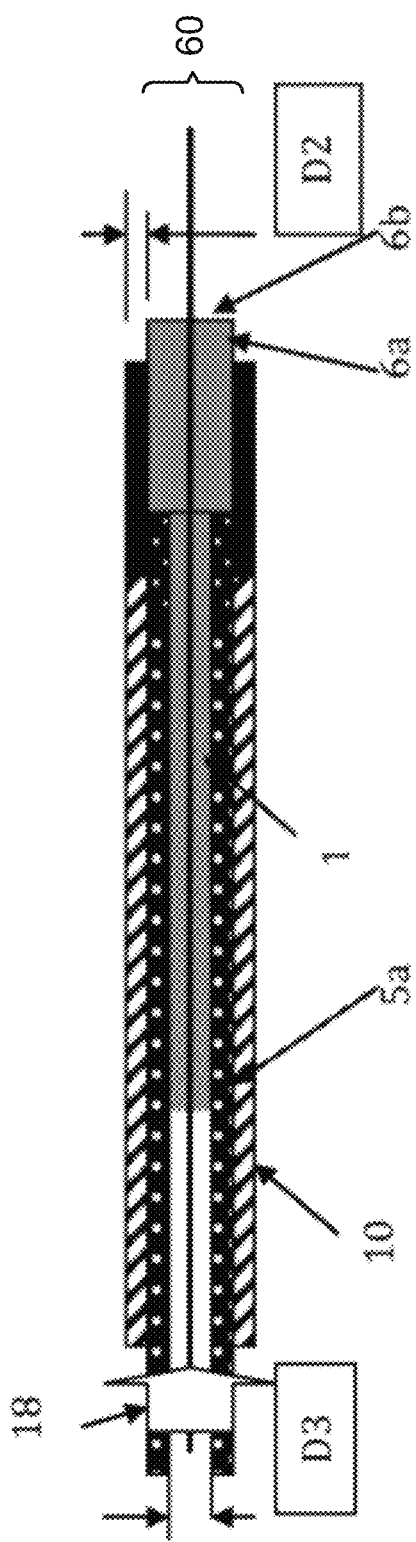

FIGS. 7A-C illustrate another embodiment of a method of the subject invention. A catheter or stent (1) is loaded or facilitated into a sheath (10) thru a loading fixture (12). A loading fixture (12) contains a lumen (23) with distal and proximal openings. The proximal opening of loading fixture (12) has an internal diameter that is greater than the external diameter of sheath (10).

The distal end of sheath (10) is inserted in the proximal opening of loading fixture (12). The proximal end of catheter (1) is then inserted into the distal opening of loading fixture (12) by applying an axial force (24) to the distal end (6b) of the bulbous or enlarged anchorage end (6a). Catheter (1) passes through the internal lumen of fixture (12) and inserts into in internal diameter (D4) of sheath (10) until the bulbous or enlarged anchorage end (6a) (collapses and) is fully contained within sheath (10). A pusher catheter (5a) has an internal lumen (not shown) in inserted into the proximal end of sheath (10). Pusher catheter (5a) has an internal diameter (D3) that is large enough to allow the outer diameter (2) of the shaft (1a) of catheter (1) to pass through pusher catheter (5a) as it advances. However, this internal lumen diameter is smaller than the outer diameter (60) of the bulbous or enlarged anchorage end (6a) of catheter (1). Thus, the distal end (5b) of pusher catheter (5a) physically engages the proximal end (6c) of the bulbous or enlarged anchorage end (6a). The catheter (1) and the bulbous or enlarged anchorage end (6a) are both coaxially contained within sheath (10). Once the anatomical site is reached, the distal end (5b) of pusher catheter (5a) physically engages the proximal end (6c) of the bulbous or enlarged anchorage end (6a) and applies an axial force (Fx) to coaxially advance the catheter (1) over the guidewire (4) in a distal direction (18) out through sheath (10).

Figure 8:
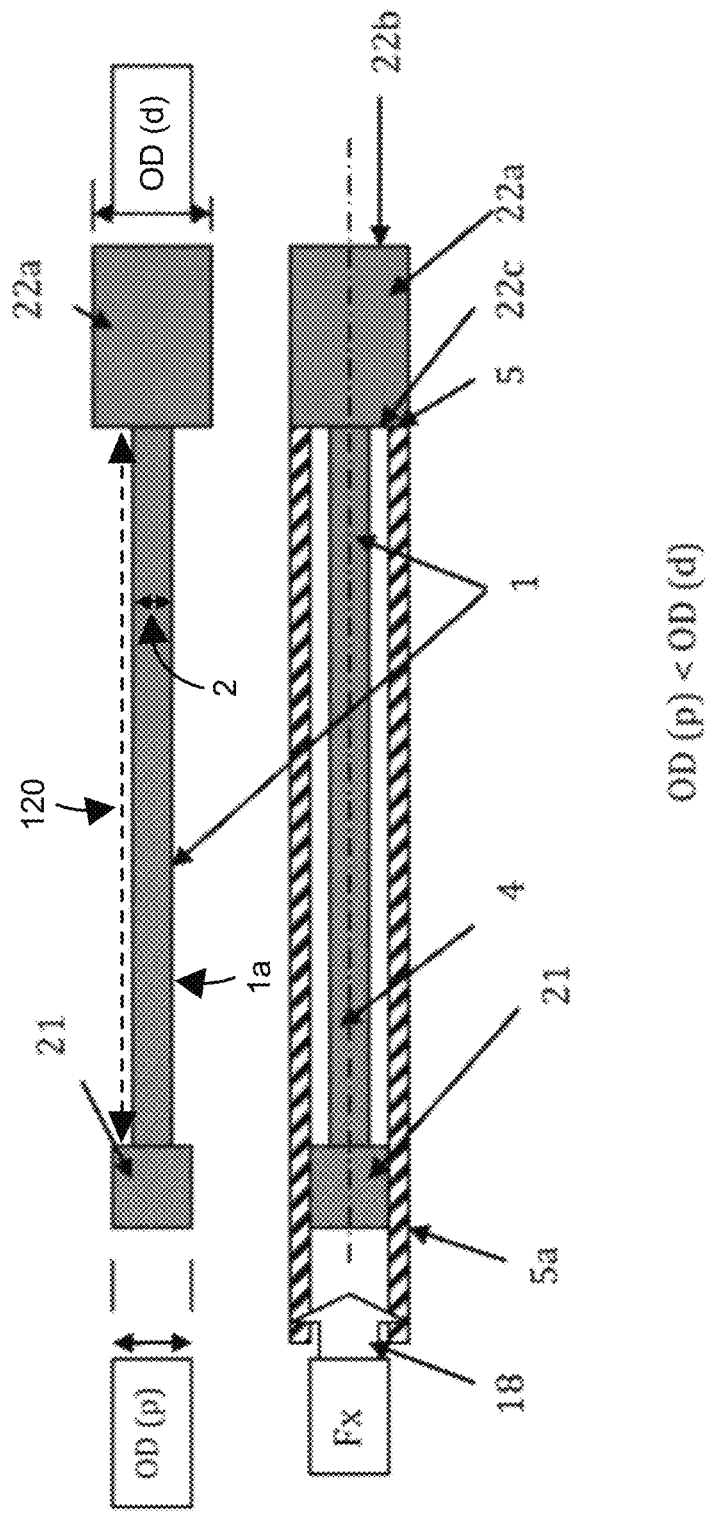
FIG. 8 illustrates a top cross-sectional view of a catheter with a bulbous or enlarged proximal end anchor and a bulbous or enlarged distal end anchor (of larger diameter than the bulbous or enlarged proximal end anchor diameter), being pushed over a guidewire by the physical engagement of the distal end of a pusher catheter and the proximal end of the bulbous or enlarged distal end anchor.

FIG. 8 illustrates a top cross-sectional view of a catheter (1) with a bulbous or enlarged proximal end anchor (21) with an outer diameter (OD (p)) and a bulbous or enlarged distal end anchor (22a) with an outer diameter (OD (d)). The distance between bulbous or enlarged proximal end anchor (21) and the bulbous or enlarged distal end anchor (22a) has a length (120) along shaft (1a) of the catheter (1). The outer diameter (OD (p)) is slightly smaller that outer diameter (OD (d)), which are both larger than the outer diameter (2) of the shaft (1a) of the catheter (1). The bulbous or enlarged distal end anchor (22a) has a distal end (22b) and a proximal end (22c).

A pusher catheter (5a) has an internal lumen (not shown) with an internal diameter that is large enough to allow the guidewire (4), the outer diameter (2) and the outer diameter (OD (p)) of the bulbous or enlarged proximal end anchor to pass through pusher catheter (5a) as it advances. However, this internal lumen diameter is smaller than the outer diameter OD (d) of the bulbous or enlarged distal end anchor (22a) of catheter (1). Thus, the distal end (5b) of pusher catheter (5a) physically engages the proximal end (22c) of the bulbous or enlarged distal end anchor (22a) and applies an axial force (Fx) to coaxially advance the catheter (1) over the guidewire (4) in a distal direction (18) through anatomical passages (not shown).

Figure 10:
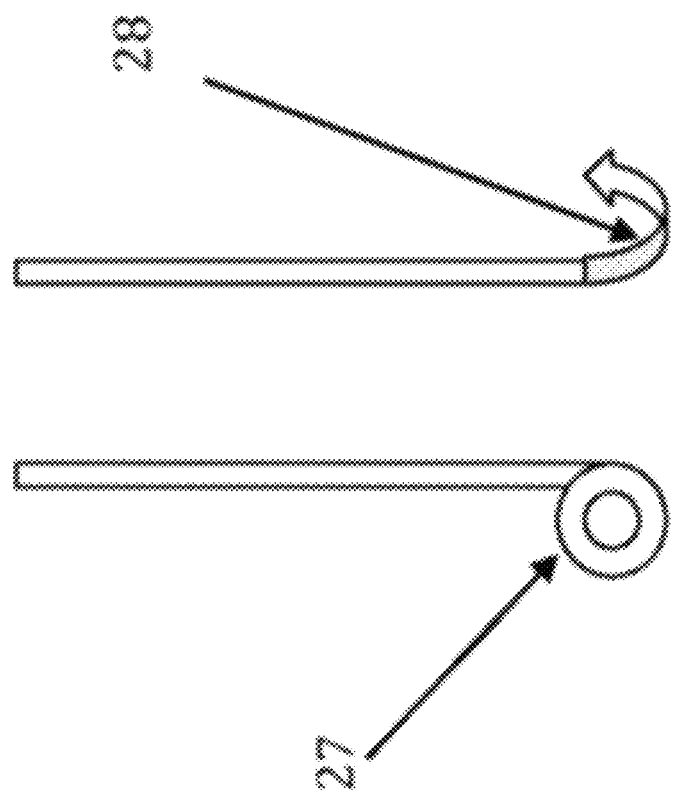
FIG. 10 illustrates a top view of a conventional pigtail loop catheter and a "J" loop catheter.

As shown in FIG. 10, Ureteral stents often have this type of proximal and distal anchorage ends. However, conventional Ureteral stents typically have an end with a spiral or "pigtail" loop (27) configuration, or a "J" shaped loop (28) configuration.

This method of delivery will reduce the pain and discomfort in patients caused by the deformation of Pigtail loop (27) and J shaped loop (28) during catheter implantation. This pain is partially due to the winding and unwinding of the pigtail loop (27) or J shaped loop (28) during implantation. Unfortunately, as these loops unwind to about half the circumference of the loop diameter, the loops become stuck in that configuration. Thereafter, the radial forces which project from the re-configured loops subject the patient to pain, and discomfort.

FIG. 11 is a flow chart 1100 of a method for delivering a catheter or stent to an anatomical site. In step 1110, a guidewire is inserted into a patient, such that a distal end of the guidewire is proximal to the anatomical site and a proximal end of the guidewire is accessible to a user. In step 1120, an internal channel of the catheter or stent is placed on the proximal end of the guidewire. The catheter or stent comprises an elongated cylindrical portion having a first diameter; a bulbous or enlarged anchorage having a second diameter greater than the first diameter, the bulbous or enlarged anchorage disposed at a distal end of the elongated cylindrical portion; and the internal channel extending along a channel axis from a proximal end of the elongated cylindrical member to a distal end of the bulbous or enlarged anchorage. In step 1130, a pusher tube is placed over a proximal end of the catheter or stent, the pusher tube having an internal lumen, the internal lumen having an internal diameter greater than the first diameter but less than the second diameter. In step 1140, an axial force to a proximal end of the pusher tube is applied, the axial force causing a wall on a distal end of the pusher tube to physically engage a proximal end of the bulbous or enlarged anchorage. In step 1150, the axial force at the proximal end of the pusher tube causes the bulbous or enlarged anchorage to advance distally along the guidewire.

In various embodiments of the subject invention, the sheath or pusher catheter may have radiopaque ends.

In other embodiments of the subject invention, the bulbous or enlarged anchorage end of the catheter or stent may have a spherical, oval, barbell, trumpet or conical profile.

In another embodiment of the subject invention, the stent or catheter used in the method may be composed entirely or partially of soft hydrogel polymer layers, such as the soft hydrogel ureteral stents disclosed in Epstein, U.S. Published Patent Application No. 2007/0106361. The contents of Epstein are incorporated herein by reference.

The devices disclosed in Epstein are composed entirely of, or have integral components, such as the bulbous or enlarged anchorage end, composed entirely of 100% hydrogel layers. Thus, the devices can comprise, consists of, or consist essentially of hydrogel layers. The hydrogel is an integral component comprising the stent or catheter, not a coating that may erode during passage through anatomical lumens.

These hydrogel devices may also be implanted with a substantially smaller diameter that is partially or totally dehydrated. In this manner, the ratio of proximal to distal diameters is typical to the fully hydrated devices whereby a pusher catheter may still coaxially slide over the proximal end diameter and engage a slightly larger distal end diameter. Upon reaching the anatomical site, these highly hydrophilic devices are then hydrated with a significant volume of an aqueous media, such as saline. Upon hydration, the hydrogel cross sections of these devices expand into predictable larger, soft, easily compressible and structurally stable shapes that maintain their mechanical integrity.

These devices do not erode and do not require a substrate or scaffold to maintain their composition or mechanical characteristics. Substantial mechanical characteristics are exhibited by fully hydrated devices, which can be loaded with colorants, radiopacifiers and fillers. These devices immediately exhibit lubricous surface characteristics when wetted with any aqueous media and provide increased resistance to biological complications, such as physiological rejection or inflammation, once implanted. The anchorage ends of these devices will not migrate will exhibit resistance to encrustation and will facilitate the ease of implant and withdrawal.

Furthermore, hybrid designs utilizing a hydrogel component and non-hydrogel components can be engineered with different percent concentrations of solids in a specific layer, or positioned specifically along the axis of a catheter shaft. In this manner, radiopaque media can be placed where it is desired, or a denser matrix can be produced in specific layers along the axis, providing a differential gradient that promotes diffusion or conduction enhancing drainage, or providing a specific drug delivery barrier.

In another embodiment of the subject invention, a low profile balloon may be integrated into the catheter, either within or external to the bulbous or enlarged anchorage end.

What is claimed is:

1. A catheter or stent delivery system comprising: a flexible catheter or stent comprising an elongated cylindrical portion having a catheter shaft length and a catheter shaft diameter, the catheter or stent terminating in an enlarged anchorage portion at a distal end thereof having an anchorage diameter greater than the catheter shaft diameter, said catheter or stent having an internal fluid channel comprising a catheter or stent lumen running through said catheter or stent from a proximal end of the elongated cylindrical portion through the distal end and enlarged anchorage portion; and an elongated pusher tube having an internal lumen running axially therethrough from a proximal to a distal end of the pusher tube, the internal lumen having an internal diameter greater than the catheter shaft diameter but less than the anchorage diameter, the pusher tube; wherein the elongated cylindrical portion of the catheter or stent is disposed within the internal lumen of the pusher tube, and wherein the distal end of the pusher tube physically contacts a proximal end of the enlarged anchorage portion of the catheter or stent, such that an axial force applied to the pusher tube causes the distal end of the pusher tube to transfer said force to said enlarged anchorage portion of the catheter or stent, wherein the delivery system is disposed in a sheath, wherein a distal end of the sheath includes axial slits, wherein the axial slits are configured to open in response to the distal advancement of the enlarged anchorage portion.

2. The delivery system of claim 1, wherein the enlarged anchorage portion has a shape selected from the group consisting of: substantially spherical, substantially ovoid, substantially barbell, substantially trumpet-shaped, and substantially conical.

3. The delivery system of claim 1, wherein the elongated cylindrical portion of the catheter or stent comprises an anchor portion disposed at the proximal end of the elongated cylindrical portion, the anchor portion configured to anchor a proximal end of the catheter or stent in an anatomical cavity.

4. The delivery system of claim 1, wherein port holes are defined in a distal end of the elongated cylindrical portion proximal to the enlarged anchorage.

5. The delivery system of claim 1, wherein the catheter or stent comprises hydrogel polymer layers.

6. A catheter or stent delivery system comprising: a catheter or stent comprising: an elongated cylindrical portion having a first external diameter; and an enlarged anchorage having a second external diameter greater than the first external diameter, the enlarged anchorage disposed at a distal end of the elongated cylindrical portion; a cylindrical pusher tube having a third external diameter less than the second external diameter; an internal channel extending along a channel axis from a proximal end of the cylindrical pusher tube to a distal end of the enlarged anchorage; a sheath having a sheath internal diameter greater than the first and third external diameters but less than the second external diameter, wherein the cylindrical pusher tube and the elongated cylindrical portion are disposed in the sheath such that a distal end of the cylindrical pusher tube physically engages a proximal end of the elongated cylindrical portion, such that an axial force at a proximal end of the cylindrical pusher tube causes the enlarged anchorage to advance distally, wherein the delivery system is disposed in the sheath, wherein a distal end of the sheath includes axial slits, wherein the axial slits are configured to open in response to the distal advancement of the enlarged anchorage.

7. The delivery system of claim 6, wherein the enlarged anchorage has a shape selected from the group consisting of: substantially spherical, substantially ovoid, substantially barbell, substantially trumpet-shaped, and substantially conical.

8. The delivery system of claim 6, wherein the elongated cylindrical portion comprises an anchor portion disposed at the proximal end of the elongated cylindrical portion, the anchor portion configured to anchor a proximal end of the catheter or stent in an anatomical cavity.

9. The delivery system of claim 6, wherein port holes are defined in a distal end of the elongated cylindrical portion proximal to the enlarged anchorage.

10. The delivery system of claim 6, wherein the catheter or stent comprises hydrogel polymer layers.

11. A method for delivering a catheter or stent to a target site through an elongated anatomical lumen, the method comprising: a) inserting a guidewire into a patient, such that a distal end of the guidewire is proximal to the target site and a proximal end of the guidewire is accessible to a user; b) placing an internal channel of the catheter or stent on the proximal end of the guidewire, the catheter or stent comprising: an elongated cylindrical portion having a first diameter; an enlarged anchorage having a second diameter greater than the first diameter, the enlarged anchorage disposed at a distal end of the elongated cylindrical portion; and the internal channel extending along a channel axis from a proximal end of the elongated cylindrical member to a distal end of the enlarged anchorage; c) placing a tubular pusher tube over a proximal end of the catheter or stent, the pusher tube having an internal lumen, the internal lumen having an internal diameter greater than the first diameter but less than the second diameter; d) applying an axial force to a proximal end of the pusher tube, the axial force causing a wall on a distal end of the pusher tube to physically engage a proximal end of the enlarged anchorage, such that the axial force at the proximal end of the pusher tube causes the enlarged anchorage to advance distally along the guidewire, wherein the catheter or stent and pusher tube are disposed in a sheath, wherein a distal end of the sheath includes axial slits, wherein the axial slits are configured to open in response to the distal advancement of the enlarged anchorage.

12. The method of claim 11, further comprising stopping the axial force when the catheter or stent is positioned proximal to the anatomical site.

13. The method of claim 12, further comprising removing the pusher tube after said catheter or stent reach the target site.

14. The method of claim 11, further comprising transferring axial insertion forces from a proximal end of said pusher tube to a distal end of said catheter or stent.

* * * * *